(12) United States Patent
Konze et al.

(10) Patent No.: US 7,288,572 B2
(45) Date of Patent: Oct. 30, 2007

(54) ACTIVE SUBSTANCE COMBINATIONS HAVING INSECTICIDAL AND ACARICIDAL PROPERTIES

(75) Inventors: Jörg Konze, Köln (DE); Wolfram Andersch, Bergisch Gladbach (DE); Dietrich Stübler, Monheim (DE); Rüdiger Fischer, Pulheim (DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 11/521,881

(22) Filed: Sep. 15, 2006

(65) Prior Publication Data

US 2007/0015835 A1 Jan. 18, 2007

Related U.S. Application Data

(62) Division of application No. 10/531,136, filed on Sep. 21, 2005, now Pat. No. 7,135,499.

(30) Foreign Application Priority Data

Oct. 16, 2002 (DE) .............................. 102 48 257

(51) Int. Cl.
| | |
|---|---|
| *A01N 37/20* | (2006.01) |
| *A01N 37/22* | (2006.01) |
| *A01N 37/28* | (2006.01) |
| *A01N 47/30* | (2006.01) |
| *A01N 47/34* | (2006.01) |

(52) U.S. Cl. .................. 514/616; 514/590; 514/594; 514/615; 514/622

(58) Field of Classification Search ................ 514/616
See application file for complete search history.

(56) References Cited

U.S. PATENT DOCUMENTS

| | | | |
|---|---|---|---|
| 4,024,163 A | 5/1977 | Elliott et al. ............. 260/347.4 |
| 4,139,636 A | 2/1979 | Sirrenberg et al. .......... 424/322 |
| 4,310,519 A | 1/1982 | Albers-Schonberg et al. ............ 424/181 |
| 4,427,663 A | 1/1984 | Mrozik ........................ 424/180 |
| 4,622,337 A | 11/1986 | Elliott et al. ................ 514/461 |
| 4,623,658 A | 11/1986 | Anderson .................... 514/482 |
| 4,666,942 A | 5/1987 | Anderson .................... 514/594 |
| 4,672,139 A | 6/1987 | Anderson .................... 560/16 |
| 4,698,365 A | 10/1987 | Anderson .................... 514/594 |
| 4,843,068 A | 6/1989 | Hamaguchi et al. .......... 514/63 |
| 4,849,432 A | 7/1989 | Shiokawa et al. .......... 514/341 |
| 4,962,126 A | 10/1990 | Drabek ........................ 514/587 |
| 5,004,822 A | 4/1991 | Elliott et al. ................ 556/115 |
| 5,034,404 A | 7/1991 | Uneme et al. .............. 514/365 |
| 5,110,986 A | 5/1992 | Kelly .......................... 564/149 |
| 5,232,940 A | 8/1993 | Hatton et al. ............... 514/407 |
| 5,362,634 A | 11/1994 | Boeck et al. ................. 435/76 |
| 5,367,093 A | 11/1994 | Dekeyser et al. ............. 560/27 |
| 5,434,181 A | 7/1995 | Kodaka et al. ............. 514/471 |
| 5,438,123 A | 8/1995 | Dekeyser et al. ........... 534/885 |
| 5,462,938 A | 10/1995 | Annus et al. ............. 514/229.8 |
| 5,478,855 A | 12/1995 | Suzuki et al. .............. 514/374 |
| 5,489,603 A | 2/1996 | Uneme et al. .............. 514/365 |
| 5,496,931 A | 3/1996 | Boeck et al. ................. 536/7.1 |
| 5,532,365 A | 7/1996 | Kodaka et al. ............. 544/212 |
| 5,536,746 A | 7/1996 | Dekeyser et al. ........... 514/468 |
| 5,547,974 A | 8/1996 | Hatton et al. ............... 514/406 |
| 5,571,901 A | 11/1996 | Boeck et al. ................. 536/7.1 |
| 5,608,077 A | 3/1997 | Hatton et al. ............. 548/365.1 |
| 5,633,375 A | 5/1997 | Uneme et al. .............. 544/336 |
| 5,708,170 A | 1/1998 | Annis et al. ................ 544/212 |
| 5,714,191 A | 2/1998 | Hatton et al. ............... 426/532 |
| 5,814,652 A | 9/1998 | Wu ............................ 514/404 |
| 5,852,012 A | 12/1998 | Maienfisch et al. ...... 514/229.2 |
| 5,883,112 A | 3/1999 | Pilato et al. ................ 514/404 |
| 5,916,618 A | 6/1999 | Hatton et al. ............... 426/532 |
| 6,015,910 A | 1/2000 | Wu ............................ 548/367.7 |
| 6,022,871 A | 2/2000 | Maienfisch et al. ...... 514/229.2 |
| 6,376,487 B1 | 4/2002 | Maienfisch et al. ...... 514/229.2 |
| 6,627,753 B1 | 9/2003 | Maienfisch et al. ........... 544/67 |
| 2003/0232821 A1 | 12/2003 | Malenfisch et al. ...... 514/229.2 |
| 2004/0077500 A1* | 4/2004 | Sakata et al. ............... 504/261 |

FOREIGN PATENT DOCUMENTS

| | | |
|---|---|---|
| CA | 2129770 | 2/1995 |
| EP | 1 006 107 | 6/2000 |
| WO | 02/087334 | 11/2002 |

OTHER PUBLICATIONS

Weeds, 15, (month unavailable) 1967, pp. 20-22, S.R. Colby, Calculating Synergistic and Antagonistic Responses of Herbicide Combinations.

* cited by examiner

*Primary Examiner*—John Pak
(74) *Attorney, Agent, or Firm*—Richard E. L. Henderson

(57) ABSTRACT

The present invention relates to novel insecticidally and acaricidally active compound combinations of $N^2$-[1,1-dimethyl-2-(methylsulphonyl)ethyl]-3-iodo-$N^1$-{2-methyl-4-[1,2,2,2-tetrafluoro-1-(trifluoromethyl)ethyl]phenyl}phthalamide of the formula (I) and active compounds identified in the disclosure.

3 Claims, No Drawings

ACTIVE SUBSTANCE COMBINATIONS HAVING INSECTICIDAL AND ACARICIDAL PROPERTIES

This application is a division of U.S. application Ser. No. 10/531,136, filed Sep. 21, 2005 now U.S. Pat. No. 7,135,499, which was filed under 35 U.S.C. 371 as a national stage application of PCT/EP2003/011022, filed Oct. 6, 2003, which was published in German as International Patent Publication WO 2004/034786 on Apr. 29, 2004, and is entitled to the right of priority of German Patent Application 102 48 257.8, filed Oct. 16, 2002.

The present invention relates to novel active compound combinations comprising the known $N^2$-[1,1-dimethyl-2-(methylsulphonyl)ethyl]-3-iodo-$N^1$-{2-methyl-4-[1,2,2,2-tetrafluoro-1-(trifluoromethyl)ethyl]phenyl}phthalamide and other known insecticidally active compounds, which combinations are highly suitable for controlling animal pests such as insects and unwanted acarids.

It is already known that $N^2$-[1,1-dimethyl-2-(methylsulphonyl)ethyl]-3-iodo-$N^1$-{2-methyl-4-[1,2,2,2-tetrafluoro-1-(trifluoromethyl)ethyl]phenyl}phthalamide has insecticidal properties (EP-A 1 006 107). The activity of this substance is good; however, at low application rates it is sometimes unsatisfactory.

Furthermore, it is already known that numerous heterocycles, benzoylureas and pyrethroids have insecticidal and acaricidal properties (cf. WO 93/22 297, WO 93/10 083, EP-A 0 210 487, EP-A 0 161 019, DE-A 26 01 780, EP-A 0 235 725, DE-A 23 26 077, EP-A 0 295 117 and EP-A 0 234 045). However, the action of these substances is not always satisfactory.

It has now been found that the novel active compound combinations of $N^2$-[1,1-dimethyl-2-(methylsulphonyl)ethyl]-3-iodo-$N^1$-{2-methyl-4-[1,2,2,2-tetrafluoro-1-(trifluoromethyl)ethyl]phenyl}phthalamide of the formula (I)

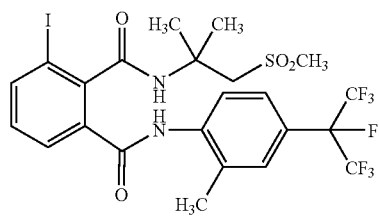
(I)

and

A) benzoylureas, preferably 1. triflumuron

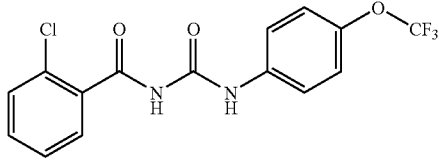

known from DE-A-26 01 780 and/or 2. flufenoxuron

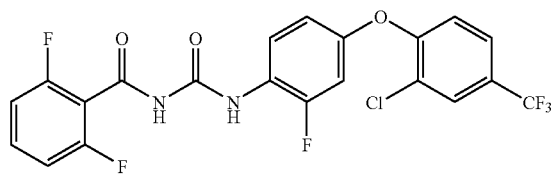

known from EP-A 0 161 019 and/or

B) diacylhydrazines, preferably 3. methoxyfenozide

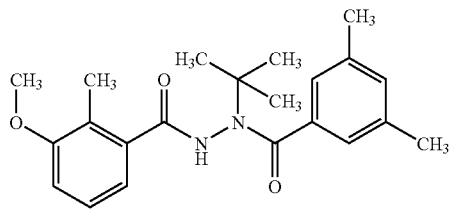

known from EP-A 0 639 559 and/or 4. tebufenozide

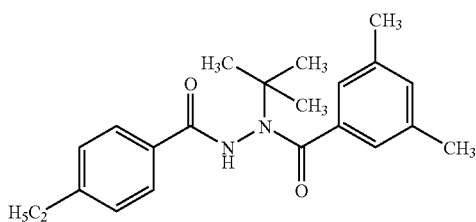

known from EP-A 0 339 854 and/or

C) chloronicotinyls, preferably 5. thiacloprid

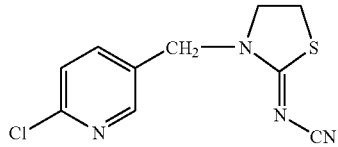

known from EP-A 0 235 725 and/or 6. thiamethoxam

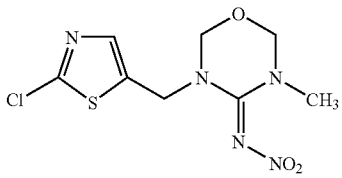

known from EP-A 0 580 553 and/or 7. dinotefuran

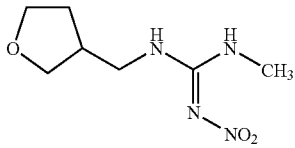

known from EP-A 0 649 845 and/or 8. clothianidin

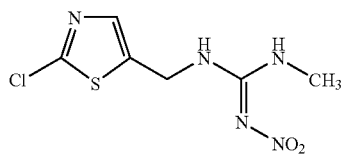

known from EP-A 0 376 279 and/or
D) pyrethroids, preferably 9. deltamethrin

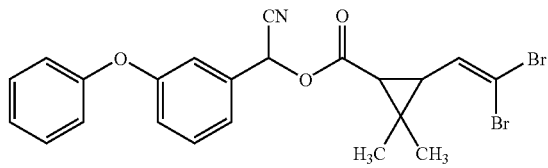

known from DE-A 23 26 077 and/or
E) phenylpyrazoles, preferably 10. ethiprole

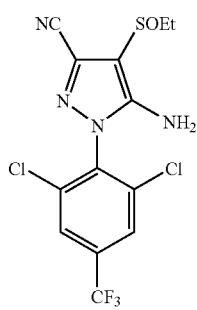

known from DE-A 196 53 417 and/or 11. fipronil

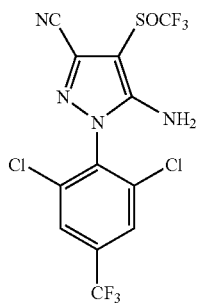

known from EP-A 0 295 117 and/or
F) carboxylates, preferably 12. indoxacarb

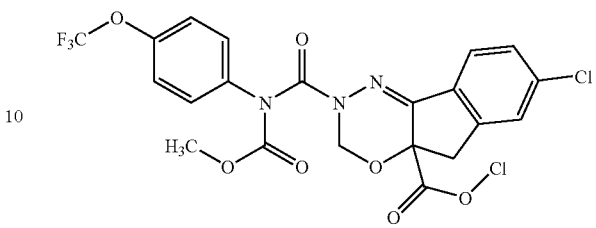

known from WO 92/11249 and/or
G) macrolides, preferably
13. emamectin-benzoate
known from EP-A 0 089 202
and/or
14. abamectin
known from DE-A 27 17 040
and/or
15. spinosad
known from EP-A 0 375 316 have very good insecticidal and acaricidal properties.

Surprisingly, the insecticidal and acaricidal activity of the active compound combination according to the invention is considerably higher than the sum of the activities of the individual active compounds. A true, unforeseeable synergistic effect is present, and not just an addition of activities.

In addition to $N^2$-[1,1-dimethyl-2-(methylsulphonyl)ethyl]-3-iodo-$N^1$-{2-methyl-4-[1,2,2,2-tetrafluoro-1-(trifluoromethyl)ethyl]phenyl}phthalamide of the formula (I), the active compound combinations according to the invention comprise at least one active compound from among compounds 1 to 15.

Preference is given to active compound combinations comprising $N^2$-[1,1-dimethyl-2-(methylsulphonyl)ethyl]-3-iodo-$N^1$-{2-methyl-4-[1,2,2,2-tetrafluoro-1-(trifluoromethyl)ethyl]phenyl}phthalamide of the formula (I) and at least one benzoylurea, selected from compounds 1 and 2.

Preference is given to active compound combinations comprising $N^2$-[1,1-dimethyl-2-(methylsulphonyl)ethyl]-3-iodo-$N^1$-{2-methyl-4-[1,2,2,2-tetrafluoro-1-(trifluoromethyl)ethyl]phenyl}phthalamide of the formula (I) and at least one diacylhydrazine, selected from compounds 3 and 4.

Preference is given to active compound combinations comprising $N^2$-[1,1-dimethyl-2-(methylsulphonyl)ethyl]-3-iodo-$N^1$-{2-methyl-4-[1,2,2,2-tetrafluoro-1-(trifluoro-methyl)ethyl]phenyl}phthalamide of the formula (I) and at least one chloronicotinyl, selected from compounds 5 to 8.

Preference is given to active compound combinations comprising $N^2$-[1,1-dimethyl-2-(methylsulphonyl)ethyl]-3-iodo-$N^1$-{2-methyl-4-[1,2,2,2-tetrafluoro-1-(trifluoromethyl)ethyl]phenyl}phthalamide of the formula (I) and deltamethrin, Preference is given to active compound combinations comprising $N^2$-[1,1-dimethyl-2-(methylsulphonyl)ethyl]-3-iodo-$N^1$-{2-methyl-4-[1,2,2,2-tetrafluoro-1-(trifluoromethyl)ethyl]phenyl}phthalamide of the formula (I) and at least one phenylpyrazole, selected from compounds 10 and 11.

Preference is given to active compound combinations comprising $N^2$-[1,1-dimethyl-2-(methylsulphonyl)ethyl]-3- iodo-$N^1$-{2-methyl-4-[1,2,2,2-tetrafluoro-1-(trifluoromethyl)ethyl]phenyl}phthalamide of the formula (I) and indoxacarb.

Preference is given to active compound combinations comprising $N^2$-[1,1-dimethyl-2-(methylsulphonyl)ethyl]-3-iodo-$N^1$-{2-methyl-4-[1,2,2,2-tetrafluoro-1-(trifluoromethyl)ethyl]phenyl}phthalamide of the formula (I) and at least one macrolide, selected from compounds 13 to 15.

Particular preference is given to active compound combinations comprising $N^2$-[1,1-dimethyl-2-(methylsulphonyl)ethyl]-3-iodo-$N^1$-{2-methyl-4-[1,2,2,2-tetrafluoro-1-(trifluoromethyl)ethyl]phenyl}phthalamide of the formula (I) and triflumuron.

Particular preference is given to active compound combinations comprising $N^2$-[1,1-dimethyl-2-(methylsulphonyl)ethyl]-3-iodo-$N^1$-{2-methyl-4-[1,2,2,2-tetrafluoro-1-(trifluoromethyl)ethyl]phenyl}phthalamide of the formula (I) and flufenoxuron.

Particular preference is given to active compound combinations comprising $N^2$-[1,1-dimethyl-2-(methylsulphonyl)ethyl]-3-iodo-$N^1$-{2-methyl-4-[1,2,2,2-tetrafluoro-1-(trifluoromethyl)ethyl]phenyl}phthalamide of the formula (I) and methoxyfenozide.

Particular preference is given to active compound combinations comprising $N^2$-[1,1-dimethyl-2-(methylsulphonyl)ethyl]-3-iodo-$N^1$-{2-methyl-4-[1,2,2,2-tetrafluoro-1-(trifluoromethyl)ethyl]phenyl}phthalamide of the formula (I) and tebufenozide.

Particular preference is given to active compound combinations comprising $N^2$-[1,1-dimethyl-2-(methylsulphonyl)ethyl]-3-iodo-$N^1$-{2-methyl-4-[1,2,2,2-tetrafluoro-1-(trifluoromethyl)ethyl]phenyl}phthalamide of the formula (I) and thiacloprid.

Particular preference is given to active compound combinations comprising $N^2$-[1,1-dimethyl-2-(methylsulphonyl)ethyl]-3-iodo-$N^1$-{2-methyl-4-[1,2,2,2-tetrafluoro-1-(trifluoromethyl)ethyl]phenyl}phthalamide of the formula (I) and thiamethoxam.

Particular preference is given to active compound combinations comprising $N^2$-[1,1-dimethyl-2-(methylsulphonyl)ethyl]-3-iodo-$N^1$-{2-methyl-4-[1,2,2,2-tetrafluoro-1-(trifluoromethyl)ethyl]phenyl}phthalamide of the formula (I) and dinotefuran.

Particular preference is given to active compound combinations comprising $N^2$-[1,1-dimethyl-2-(methylsulphonyl)ethyl]-3-iodo-$N^1$-{2-methyl-4-[1,2,2,2-tetrafluoro-1-(trifluoromethyl)ethyl]phenyl}phthalamide of the formula (I) and clothianidin.

Particular preference is given to active compound combinations comprising $N^2$-[1,1-dimethyl-2-(methylsulphonyl)ethyl]-3-iodo-$N^1$-{2-methyl-4-[1,2,2,2-tetrafluoro-1-(trifluoromethyl)ethyl]phenyl}phthalamide of the formula (I) and ethiprole.

Particular preference is given to active compound combinations comprising $N^2$-[1,1-dimethyl-2-(methylsulphonyl)ethyl]-3-iodo-$N^1$-{2-methyl-4-[1,2,2,2-tetrafluoro-1-(trifluoromethyl)ethyl]phenyl}phthalamide of the formula (I) and fipronil.

Particular preference is given to active compound combinations comprising $N^2$-[1,1-dimethyl-2-(methylsulphonyl)ethyl]-3-iodo-$N^1$-{2-methyl-4-[1,2,2,2-tetrafluoro-1-(trifluoromethyl)ethyl]phenyl}phthalamide of the formula (I) and emamectin-benzoate.

Particular preference is given to active compound combinations comprising $N^2$-[1,1-dimethyl-2-(methylsulphonyl)ethyl]-3-iodo-$N^1$-{2-methyl-4-[1,2,2,2-tetrafluoro-1-(trifluoromethyl)ethyl]phenyl}phthalamide of the formula (I) and abamectin.

Particular preference is given to active compound combinations comprising $N^2$-[1,1-dimethyl-2-(methylsulphonyl)ethyl]-3-iodo-$N^1$-{2-methyl-4-[1,2,2,2-tetrafluoro-1-(trifluoromethyl)ethyl]phenyl}phthalamide of the formula (I) and spinosad.

In addition, the active compound combinations may also comprise further fungicidally, acaricidally or insecticidally active mixing components.

If the active compounds in the active compound combinations according to the invention are present in certain weight ratios, the synergistic effect is particularly pronounced. However, the weight ratios of the active compounds in the active compound combinations can be varied within a relatively wide range. In general, the combinations according to the invention comprise the active compound $N^2$-[1,1-dimethyl-2-(methylsulphonyl)ethyl]-3-iodo-$N^1$-{2-methyl-4-[1,2,2,2-tetrafluoro-1-(trifluoromethyl)ethyl]phenyl}phthalamide of the formula (I) and the mixing partners in the preferred, particularly preferred and very particularly preferred mixing ratios stated in the table below:

The mixing ratios are based on weight ratios. The ratio is to be understood as meaning active compound of the formula (I):mixing partner:

| | Mixing partner | Preferred | Particularly preferred | Very particularly preferred |
|---|---|---|---|---|
| 1 | triflumuron | 10:1 to 1:150 | 5:1 to 1:50 | 1:1 to 1:5 |
| 2 | flufenoxuron | 10:1 to 1:50 | 5:1 to 1:25 | 1:1 to 1:5 |
| 3 | methoxyfenozide | 10:1 to 1:50 | 5:1 to 1:30 | 1:1 to 1:15 |
| 4 | tebufenozide | 10:1 to 1:50 | 5:1 to 1:30 | 1:1 to 1:15 |
| 5 | thiacloprid | 200:1 to 1:100 | 150:1 to 1:25 | 50:1 to 1:5 |
| 6 | thiamethoxam | 200:1 to 1:100 | 150:1 to 1:25 | 50:1 to 1:5 |
| 7 | dinotefuran | 200:1 to 1:100 | 150:1 to 1:25 | 50:1 to 1:5 |
| 8 | clothianidin | 1000:1 to 1:150 | 500:1 to 1:50 | 250:1 to 1:25 |
| 9 | deltamethrin | 50:1 to 1:10 | 25:1 to 1:5 | 5:1 to 1:1 |
| 10 | ethiprole | 10:1 to 1:150 | 5:1 to 1:50 | 1:1 to 1:5 |
| 11 | fipronil | 100:1 to 1:100 | 10:1 to 1:10 | 5:1 to 1:5 |
| 12 | indoxacarb | 100:1 to 1:100 | 10:1 to 1:10 | 5:1 to 1:5 |
| 13 | emamectin-benzoate | 50:1 to 1:10 | 25:1 to 1:5 | 5:1 to 1:1 |
| 14 | abamectin | 50:1 to 1:100 | 25:1 to 1:50 | 5:1 to 1:25 |
| 15 | spinosad | 50:1 to 1:10 | 25:1 to 1:5 | 5:1 to 1:1 |

The active compound combinations according to the invention are suitable for controlling animal pests, preferably arthropods and nematodes, in particular insects and arachnids, found in agriculture, in animal health, in forests, in gardens and leisure facilities in the protection of stored products and materials and in the hygiene sector, while exhibiting good tolerability to plants, low toxicity to warm-blooded species and good environmental compatibility. They are active against normally sensitive and resistant species, and against all or individual developmental stages. The abovementioned pests include:

From the order of the Isopoda, for example, *Oniscus asellus, Armadillidium vulgare, Porcellio scaber.*

From the order of the Diplopoda, for example, *Blaniulus guttulatus.*

From the order of the Chilopoda, for example, *Geophilus carpophagus, Scutigera* spp.

From the order of the Symphyla, for example, *Scutigerella immaculata.*

From the order of the Thysanura, for example, *Lepisma saccharina*.

From the order of the Collembola, for example, *Onychiurus armatus*.

From the order of the Orthoptera, for example, *Acheta domesticus*, *Gryllotalpa* spp., *Locusta migratoria migratorioides*, *Melanoplus* spp., *Schistocerca gregaria*.

From the order of the Blattaria, for example, *Blatta orientalis*, *Periplaneta americana*, *Leucophaea maderae*, *Blattella germanica*.

From the order of the Dermaptera, for example, *Forficula auricularia*.

From the order of the Isoptera, for example, *Reticulitermes* spp.

From the order of the Phthiraptera, for example, *Pediculus humanus corporis*, *Haematopinus* spp., *Linognathus* spp., *Trichodectes* spp., *Damalinia* spp.

From the order of the Thysanoptera, for example, *Hercinothrips femoralis*, *Thrips tabaci*, *Thrips palmi*, *Frankliniella accidentalis*.

From the order of the Heteroptera, for example, *Eurygaster* spp., *Dysdercus intermedius*, *Piesma quadrata*, *Cimex lectularius*, *Rhodnius prolixus*, *Triatoma* spp. From the order of the Homoptera, for example, *Aleurodes brassicae*, *Bemisia tabaci*, *Trialeurodes vaporariorum*, *Aphis gossypii*, *Brevicoryne brassicae*, *Cryptomyzus ribis*, *Aphis fabae*, *Aphis pomi*, *Eriosoma lanigerum*, *Hyalopterus arundinis*, *Phylloxera vastatrix*, *Pemphigus* spp., *Macrosiphum avenae*, *Myzus* spp., *Phorodon humuli*, *Rhopalosiphum padi*, *Empoasca* spp., *Euscelis bilobatus*, *Nephotettix cincticeps*, *Lecanium comi*, *Saissetia oleae*, *Laodelphax striatellus*, *Nilaparvata lugens*, *Aonidiella aurantii*, *Aspidiotus hederae*, *Pseudococcus* spp., *Psylla* spp.

From the order of the Lepidoptera, for example, *Pectinophora gossypiella*, *Bupalus piniarius*, *Cheimatobia brumata*, *Lithocolletis blancardella*, *Hyponomeuta padella*, *Plutella xylostella*, *Malacosoma neustria*, *Euproctis chrysorrhoea*, *Lymantria* spp., *Bucculatrix thurberiella*, *Phyllocnistis citrella*, *Agrotis* spp., *Euxoa* spp., *Feltia* spp., *Earias insulana*, *Heliothis* spp., *Mamestra brassicae*, *Panolis flammea*, *Spodoptera* spp., *Trichoplusia ni*, *Carpocapsa pomonella*, *Pieris* spp., *Chilo* spp., *Pyrausta nubilalis*, *Ephestia kuehniella*, *Galleria mellonella*, *Tineola bisselliella*, *Tinea pellionella*, *Hofmannophila pseudospretella*, *Cacoecia podana*, *Capua reticulana*, *Choristoneura fumiferana*, *Clysia ambiguella*, *Homona magnanima*, *Tortrix viridana*, *Cnaphalocerus* spp., *Oulema oryzae*.

From the order of the Coleoptera, for example, *Anobium punctatum*, *Rhizopertha dominica*, *Bruchidius obtectus*, *Acanthoscelides obtectus*, *Hylotrupes bajulus*, *Agelastica alni*, *Leptinotarsa decemlineata*, *Phaedon cochleariae*, *Diabrotica* spp., *Psylliodes chrysocephala*, *Epilachna varivestis*, *Atomaria* spp., *Oryzaephilus surinamensis*, *Anthonomus* spp., *Sitophilus* spp., *Otiorrhynchus sulcatus*, *Cosmopolites sordidus*, *Ceuthorrhynchus assimilis*, *Hypera postica*, *Derrnestes* spp., *Trogoderma* spp., *Anthrenus* spp., *Attagenus* spp., *Lyctus* spp., *Meligethes aeneus*, *Ptinus* spp., *Niptus hololeucus*, *Gibbium psylloides*, *Tribolium* spp., *Tenebrio molitor*, *Agriotes* spp., *Conoderus* spp., *Melolontha melolontha*, *Amphimallon solstitialis*, *Costelytra zealandica*, *Lissorhoptrus oryzophilus*.

From the order of the Hymenoptera, for example, *Diprion* spp., *Hoplocampa* spp., *Lasius* spp., *Monomorium pharaonis*, *Vespa* spp.

From the order of the Diptera, for example, *Aedes* spp., *Anopheles* spp., *Culex* spp., *Drosophila melanogaster*, *Musca* spp., *Fannia* spp., *Calliphora erythrocephala*, *Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus*, *Oscinella frit*, *Phorbia* spp., *Pegomyia hyoscyami*, *Ceratitis capitata*, *Dacus oleae*, *Tipula paludosa*, *Hylemyia* spp., *Liriomyza* spp.

From the order of the Siphonaptera, for example, *Xenopsylla cheopis*, *Ceratophyllus* spp.

From the class of the Arachnida, for example, *Scorpio maurus*, *Latrodectus mactans*, *Acarus siro*, *Argas* spp., *Ornithodoros* spp., *Dermanyssus gallinae*, *Eriophyes ribis*, *Phyllocoptruta oleivora*, *Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa*, *Panonychus* spp., *Tetranychus* spp., *Hemitarsonemus* spp., *Brevipalpus* spp.

The plant-parasitic nematodes include, for example, *Pratylenchus* spp., *Radopholus similis*, *Ditylenchus dipsaci*, *Tylenchulus semipenetrans*, *Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

The active compound combinations according to the invention of the compound of the formula (I) and at least one compound 1 to 15 are particularly suitable for controlling "biting" pests. These include, in particular, the following pests: From the order of the Lepidoptera for example, *Pectinophora gossypiella*, *Bupalus piniarius*, *Cheimatobia brumata*, *Lithocolletis blancardella*, *Hyponomeuta padella*, *Plutella xylostella*, *Malacosoma neustria*, *Euproctis chrysorrhoea*, *Lymantria* spp., *Bucculatrix thurberiella*, *Phyllocnistis citrella*, *Agrotis* spp., *Euxoa* spp., *Feltia* spp., *Earias insulana*, *Heliothis* spp., *Mamestra brassicae*, *Panolis flammea*, *Spodoptera* spp., *Trichoplusia ni*, *Carpocapsa pomonella*, *Pieris* spp., *Chilo* spp., *Pyrausta nubilalis*, *Ephestia kuehniella*, *Galleria mellonella*, *Tineola bisselliella*, *Tinea pellionella*, *Hofmannophila pseudospretella*, *Cacoecia podana*, *Capua reticulana*, *Choristoneura fumiferana*, *Clysia ambiguella*, *Homona magnanima*, *Tortrix viridana*, *Cnaphalocerus* spp., *Oulema oryzae*.

From the order of the Coleoptera, for example, *Anobium punctatum*, *Rhizopertha dominica*, *Bruchidius obtectus*, *Acanthoscelides obtectus*, *Hylotrupes bajulus*, *Agelastica alni*, *Leptinotarsa decemlineata*, *Phaedon cochleariae*, *Diabrotica* spp., *Psylliodes chrysocephala*, *Epilachna varivestis*, *Atomaria* spp., *Oryzaephilus surinamensis*, *Anthonomus* spp., *Sitophilus* spp., *Otiorrhynchus sulcatus*, *Cosmopolites sordidus*, *Ceuthorrhynchus assimilis*, *Hypera postica*, *Dermestes* spp., *Trogoderma* spp., *Anthrenus* spp., *Attagenus* spp., *Lyctus* spp., *Meligethes aeneus*, *Ptinus* spp., *Niptus hololeucus*, *Gibbium psylloides*, *Tribolium* spp., *Tenebrio molitor*, *Agriotes* spp., *Conoderus* spp., *Melolontha melolontha*, *Amphimallon solstitialis*, *Costelytra zealandica*, *Lissorhoptrus oryzophilus*.

The active compound combinations according to the invention of the compound of the formula (I) and at least one compound 5 to 8 are additionally particularly suitable for controlling "sucking" pests. These include, in particular, the following pests: From the order of the Homoptera, for example, *Aleurodes brassicae*, *Bemisia tabaci*, *Trialeurodes vaporariorum*, *Aphis gossypii*, *Brevicoryne brassicae*, *Cryptomyzus ribis*, *Aphis fabae*, *Aphis pomi*, *Eriosoma lanigerum*, *Hyalopterus arundinis*, *Phylloxera vastatrix*, *Pemphigus* spp., *Macrosiphum avenae*, *Myzus* spp., *Phorodon humuli*, *Rhopalosiphum padi*, *Empoasca* spp., *Euscelis bilobatus*, *Nephotettix cincticeps*, *Lecanium comi*, *Saissetia*

*oleae, Laodelphax striatellus, Nilaparvata lugens, Aonidiella aurantii, Aspidiotus hederae, Pseudococcus* spp., *Psylla* spp.

The active compound combinations according to the invention have, in particular, excellent activity against caterpillars, beetle larvae, spider mites, aphids and leaf-mining flies.

The active compound combinations according to the invention can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants, and/or foam formers.

If the extender used is water, it is also possible, for example, to use organic solvents as cosolvents. The following are essentially suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Suitable solid carriers are: for example ammonium salts and ground natural minerals such as kaolins, clays, talc, chalk, quartz, attapulgite, montmorillonite or diatomaceous earth, and ground synthetic materials such as finely divided silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

The active compound combinations according to the invention can be present in their commercially available formulations and in the use forms, prepared from these formulations, as a mixture with other active compounds, such as insecticides, attractants, sterilants, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

Mixtures with other known active compounds such as herbicides or with fertilizers and growth regulators are also possible.

When used as insecticides, the active compound combinations according to the invention can furthermore be present in their commercially available formulations and in the use forms, prepared from these formulations, as a mixture with synergists. Synergists are compounds which increase the action of the active compounds, without it being necessary for the synergist added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms. When used against hygiene pests and stored-product pests, the active compound combinations are distinguished by an excellent residual action on wood and clay as well as good stability to alkali on limed substrates.

The active compound combinations according to the invention are not only active against plant pests, hygiene pests and stored-product pests, but also, in the veterinary medicine sector, against animal parasites (ectoparasites) such as hard ticks, soft ticks, mange mites, harvest mites, flies (stinging and licking), parasitizing fly larvae, lice, head lice, bird lice and fleas. These parasites include:

From the order of the Anoplurida, for example, *Haematopinus* spp., *Linognathus* spp., *Pediculus* spp.,*Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp., *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattella germanica, Supella* spp.

From the subclass of the Acaria (*Acarida*) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compound combinations according to the invention are also suitable for controlling arthropods which attack agricultural livestock such as, for example, cattle, sheep, goats, horses, pigs, donkeys, camels, buffaloes, rabbits, chickens, turkeys, ducks, geese, honey-bees, other domestic animals such as, for example, dogs, cats, caged birds, aquarium fish and so-called experimental animals such as, for example, hamsters, guinea pigs, rats and mice. By controlling these arthropods, cases of death and reductions in productivity (for meat, milk, wool, hides, eggs, honey and the like) should be diminished, so that more economical and simpler animal husbandry is possible by the use of the active compound combinations according to the invention.

The active compound combinations according to the invention are used in the veterinary sector in a known manner by enteral administration in the form of, for example, tablets, capsules, potions, drenches, granules, pastes, boluses, the feed-through method, suppositories, by parenteral administration such as, for example, by injections (intramuscularly, subcutaneously, intravenously, intraperitoneally and the like), implants, by nasal administration, by dermal administration in the form of, for example, immersing or dipping, spraying, pouring-on, spotting-on, washing, dusting, and with the aid of active-compound-comprising moulded articles such as collars, ear tags, tail tags, limb bands, halters, marking devices and the like.

When used for cattle, poultry, domestic animals and the like, the active compound combinations can be applied as formulations (for example powders, emulsions, flowables) comprising the active compounds in an amount of 1 to 80% by weight, either directly or after 100- to 10,000-fold dilution, or they may be used as a chemical dip.

Moreover, it has been found that the active compound combinations according to the invention show a potent insecticidal action against insects which destroy industrial materials.

The following insects may be mentioned by way of example and with preference, but not by way of limitation:

Beetles such as *Hylotrupes bajulus, Chlorophorus pilosis, Anobium punctatum, Xestobium rufovillosum, Ptilinus pecticomis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus.*

Dermapterans such as *Sirex juvencus, Urocerus gigas, Urocerus gigas taignus, Urocerus augur.*

Termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.* Bristle-tails such as *Lepisma saccharina.*

Industrial materials in the present context are understood as meaning non-living materials such as, preferably, polymers, adhesives, glues, paper and board, leather, wood, timber products and paints.

The material which is to be protected from insect attack is very particularly preferably wood and timber products.

Wood and timber products which can be protected by the composition according to the invention, or mixtures comprising it, are to be understood as meaning, for example:

Construction timber, wooden beams, railway sleepers, bridge components, jetties, vehicles made of wood, boxes, pallets, containers, telephone poles, wood lagging, windows and doors made of wood, plywood, chipboard, joinery, or timber products which quite generally are used in house construction or building joinery.

The active compound combinations can be used as such, in the form of concentrates or generally customary formulations such as powders, granules, solutions, suspensions, emulsions or pastes.

The abovementioned formulations can be prepared in a manner known per se, for example by mixing the active compounds with at least one solvent or diluent, emulsifier, dispersant and/or binder or fixative, water repellant, if desired desiccants and UV stabilizers, and if desired colorants and pigments and other processing auxiliaries.

The insecticidal compositions or concentrates used for protecting wood and timber products comprise the active compound according to the invention in a concentration of 0.0001 to 95% by weight, in particular 0.001 to 60% by weight.

The amount of composition or concentrate employed depends on the species and the abundance of the insects and on the medium. The optimal quantity to be employed can be determined in each case by test series upon application. In general, however, it will suffice to employ 0.0001 to 20% by weight, preferably 0.001 to 10% by weight, of the active compound, based on the material to be protected.

A suitable solvent and/or diluent is an organochemical solvent or solvent mixture and/or an oily or oil-type organochemical solvent or solvent mixture of low volatility and/or a polar organochemical solvent or solvent mixture and/or water and, if appropriate, an emulsifier and/or wetter.

Organochemical solvents which are preferably employed are oily or oil-type solvents with an evaporation number of above 35 and a flash point of above 30° C., preferably above 45° C. Such oily and oil-type solvents which are insoluble in water and of low volatility and which are used are suitable mineral oils or their aromatic fractions or mineral-oil-containing solvent mixtures, preferably white spirit, petroleum and/or alkylbenzene.

Mineral oils with a boiling range of 170 to 220° C., white spirit with a boiling range of 170 to 220° C., spindle oil with a boiling range of 250 to 350° C., petroleum and aromatics with a boiling range of 160 to 280° C., oil of turpentine, and the like are advantageously used.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-type solvents of low volatility and with an evaporation number of above 35 and a flash point of above 30° C., preferably above 45° C., can be replaced in part by organochemical solvents of high or medium volatility, with the proviso that the solvent mixture also has an evaporation number of above 35 and a flash point of above 30° C., preferably above 45° C., and that the mixture is soluble or emulsifiable in this solvent mixture.

In a preferred embodiment, some of the organochemical solvent or solvent mixture is replaced by an aliphatic polar organochemical solvent or solvent mixture. Aliphatic organochemical solvents which contain hydroxyl and/or ester and/or ether groups are preferably used, such as, for example, glycol ethers, esters or the like. Organochemical binders used for the purposes of the present invention are the synthetic resins and/or binding drying oils which are known per se and which can be diluted in water and/or dissolved or dispersed or emulsified in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin such as indene/coumarone resin, silicone resin, drying vegetable and/or drying oils and/or physically drying binders based on a natural and/or synthetic resin.

The synthetic resin employed as binder can be employed in the form of an emulsion, dispersion or solution. Bitumen or bituminous substances may also be used as binders, in amounts of up to 10% by weight. In addition, colorants, pigments, water repellants, odour-masking agents, and inhibitors or anticorrosive agents and the like, all of which are known per se, can be employed.

In accordance with the invention, the composition or the concentrate preferably comprises, as organochemical binders, at least one alkyd resin or modified alkyd resin and/or a drying vegetable oil. Alkyd resins which are preferably used in accordance with the invention are those with an oil content of over 45% by weight, preferably 50 to 68% by weight.

Some or all of the abovementioned binder can be replaced by a fixative (mixture) or plasticizer (mixture). These additives are intended to prevent volatilization of the active compounds, and also crystallization or precipitation. They preferably replace 0.01 to 30% of the binder (based on 100% of binder employed).

The plasticizers are from the chemical classes of the phthalic esters, such as dibutyl phthalate, dioctyl phthalate or benzyl butyl phthalate, phosphoric esters such as tributyl phosphate, adipic esters such as di-(2-ethylhexyl)-adipate, stearates such as butyl stearate or amyl stearate, oleates such as butyl oleate, glycerol ethers or higher-molecular-weight glycol ethers, glycerol esters and p-toluenesulphonic esters.

Fixatives are based chemically on polyvinyl alkyl ethers such as, for example, polyvinyl methyl ether, or ketones such as benzophenone and ethylenebenzophenone.

Other suitable solvents or diluents are, in particular, water, if appropriate as a mixture with one or more of the abovementioned organochemical solvents or diluents, emulsifiers and dispersants.

Particularly effective timber protection is achieved by industrial-scale impregnating processes, for example the vacuum, double-vacuum or pressure processes.

The active compound combinations according to the invention can at the same time be employed for protecting objects which come into contact with saltwater or brackish water, such as hulls, screens, nets, buildings, moorings and signalling systems, against fouling.

Fouling by sessile Oligochaeta, such as Serpulidae, and by shells and species from the ledamorpha group (goose barnacles), such as various *Lepas* and *Scalpellum* species, or by species from the Balanomorpha group (acom barnacles), such as *Balanus* or *Pollicipes* species, increases the frictional drag of ships and, as a consequence, leads to a marked increase in operation costs owing to higher energy consumption and additionally frequent stops in the dry dock.

Apart from fouling by algae, for example *Ectocarpus* sp. and *Ceramium* sp., fouling by sessile Entomostraka groups, which come under the generic term Cirripedia (cirriped crustaceans), is of particular importance.

Surprisingly, it has now been found that the active compound combinations according to the invention have an outstanding antifouling action.

Using the active compound combinations according to the invention allows the use of heavy metals such as, for example, in bis(trialkyltin) sulphides, tri-n-butyltin laurate, tri-n-butyltin chloride, copper(I) oxide, triethyltin chloride, tri-n-butyl(2-phenyl-4-chlorophenoxy)tin, tributyltin oxide, molybdenum disulphide, antimony oxide, polymeric butyl titanate, phenyl-(bispyridine)-bismuth chloride, tri-n-butyl-tin fluoride, manganese ethylenebisthiocarbamate, zinc dimethyldithiocarbamate, zinc ethylenebisthiocarbamate, zinc salts and copper salts of 2-pyridinethiol 1-oxide, bisdimethyldithiocarbamoylzinc ethylenebisthiocarbamate, zinc oxide, copper(I) ethylene-bisdithiocarbamate, copper thiocyanate, copper naphthenate and tributyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferable suitable components in combinations with the antifouling compositions according to the invention are:

algicides such as 2-tert-butylamino-4-cyclopropylamino-6-methylthio-1,3,5-triazine, dichlorophen, diuron, endothal, fentin acetate, isoproturon, methabenzthiazuron, oxy-fluorfen, quinoclamine and terbutryn;

fungicides such as benzo[b]thiophenecarboxylic acid cyclohexylamide S,S-dioxide, dichlofluanid, fluorfolpet, 3-iodo-2-propinyl butylcarbamate, tolylfluanid and azoles such- as azaconazole, cyproconazole, epoxyconazole, hexaconazole, metconazole, propiconazole and tebuconazole;

molluscicides such as fentin acetate, metaldehyde, methiocarb, niclosamid, thiodicarb and trimethacarb;

or conventional antifouling active compounds such as 4,5-dichloro-2-octyl-4-isothiazolin-3-one, diiodomethylparatryl sulphone, 2-(N,N-dimethyl-thiocarbamoylthio)-5-nitrothiazy, potassium, copper, sodium and zinc salts of 2-pyridinethiol 1-oxide, pyridine-triphenylborane, tetrabutyldistannoxane, 2,3,5,6-tetrachloro-4-(methylsulphonyl)-pyridine, 2,4,5,6-tetrachloroisophthalonitrile, tetramethylthiuram disulphide and 2,4,6-trichlorophenylmaleiimide.

The antifouling compositions used comprise the active compound combinations according to the invention in a concentration of 0.001 to 50% by weight, in particular 0.01 to 20% by weight.

Moreover, the antifouling compositions according to the invention comprise the customary components such as, for example, those described in Ungerer, *Chem. Ind.* 1985, 37, 730-732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as colophonium to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compound combinations are also suitable for controlling animal pests, in particular insects, arachnids and mites, which are found in enclosed spaces such as, for example, dwellings, factory halls, offices, vehicle cabins and the like. They can be employed in domestic insecticide products for controlling these pests. They are active against sensitive and resistant species and against all developmental stages. These pests include:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, *Aviculariidae, Araneidae*.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Phthirus pubis*.

From the order of the Heteroptera, for example, *Cimex hemipterus, Cimex lectularius, Rhodinus prolixus, Triatoma infestans*.

They are used as aerosols, pressureless spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

According to the invention, it is possible to treat all plants and parts of plants. Plants are to be understood here as meaning all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment according to the invention of the plants and parts of plants with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferred and to be treated according to the invention include all plants which, in the genetic modification, received genetic material which imparts particularly advantageous useful traits to these plants. Examples of such traits are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are particularly emphasized are the increased defence of the plants against insects, arachnids, nematodes and worms by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are also particularly emphasized are the increased defence of plants against fungi, bacteria and viruses by systemic acquired resistance (SAR), systemin, phytoalexins, elicitors and also resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes in question which impart the desired traits can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink(® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready(® (tolerance to glyphosate, for example maize, cotton, soya beans), Liberty Link(® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these or still-to-be-developed genetic traits, which plants will be developed and/or marketed in the future.

The plants listed can be treated according to the invention in a particularly advantageous manner with the active compound mixtures according to the invention. The preferred ranges stated above for the mixtures also apply to the treatment of these plants. Particular emphasis is given to the treatment of plants with the mixtures specifically mentioned in the present text.

The good insecticidal and acaricidal action of the active compound combinations according to the invention can be seen from the examples which follow. While the individual active compounds show weaknesses in their action, the combinations show an action which exceeds a simple sum of actions.

A synergistic effect in insecticides and acaricides is always present when the action of the active compound combinations exceeds the total of the actions of the active compounds when applied individually.

The expected action for a given combination of two active compounds can be calculated as follows, using "Colby's formula" (cf. S. R. Colby, "Calculating Synergistic and Antagonistic Responses of Herbicide Combinations", Weeds 1967, 15, 20-22):

If

X is the kill rate, expressed as a percentage of the untreated control, when employing active compound A at an application rate of m g/ha or in a concentration of m ppm, Y is the kill rate, expressed as a percentage of the untreated control, when employing active compound B at an application rate of n g/ha or in a concentration of n ppm and E is the kill rate, expressed as a percentage of the untreated control, when employing active compounds A and B at application rates of m and n g/ha or in a concentration of m and n ppm, then $$E = X + Y - \frac{X \cdot Y}{100}$$

If the actual insecticidal kill rate exceeds the calculated value, the action of the combination is superadditive, i.e. a synergistic effect is present. In this case, the actually observed kill rate must exceed the value calculated using the above formula for the expected kill rate (E).

USE EXAMPLES

In all use examples, the compound $N^2$-[1,1-dimethyl-2-(methylsulphonyl)ethyl]-3-iodo-$N^1$-{2-methyl-4-[1,2,2,2-tetrafluoro-1-(trifluoromethyl)ethyl]phenyl}-phthalamide of the formula (I) is referred to in short as "(I)".

Example A

| *Aphis gossypii* test | |
|---|---|
| Solvent: | 7 parts by weight of dimethylformamide |
| Emulsifier: | 2 parts by weight of alkylaryl polyglycol ether |

To produce a suitable preparation of active compound, 1 part b, weight of active compound is mixed with the stated amounts of solvent and emulsifier, and the concentrate is diluted with water to the desired concentrations.

Cotton leaves (*Gossypium hirsutum*) which are heavily infested by the cotton aphid (*Aphis gossypii*) are treated by being dipped into the preparation of active compound of the desired concentration.

After the desired period of time, the kill in % is determined. 100% means that all aphids have been killed; 0% means that none of the aphids have been killed. The determined kill rates are calculated using Colby's formula (see page 29).

In this test, for example, the following active compound combination according to the present application shows a synergistically enhanced activity, compared to the active compounds applied on their own:

TABLE A

| | Plant-damaging insects *Aphis gossypii* test | | |
|---|---|---|---|
| | Concentration of active compound | Kill rate in % after 6$^d$ | |
| Active compounds | in ppm | found* | calc.** |
| thiacloprid | 3 | 50 | |
| (I) | 500 | 0 | |
| thiacloprid + (I) (1:167) | 3 + 500 | 80 | 50 |

*found = activity found
**calc. = activity calculated using Colby's formula

Example B

| *Myzus* test | |
|---|---|
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) which are heavily infested by the green peach aphid (*Myzus persicea*) are treated by being dipped into the preparation of active compound of the desired concentration.

After the desired period of time, the kill in % is determined. 100% means that all aphids have been killed; 0% means that none of the aphids have been killed. The determined kill rates are calculated using Colby's formula (see page 29).

In this test, for example, the following active compound combination according to the present application shows a synergistically enhanced activity, compared to the active compounds applied on their own:

TABLE B

| | Plant-damaging insects *Myzus* test | | | |
|---|---|---|---|---|
| | Concentration of active | Kill rate in % after d | | |
| Active compounds | compound in ppm | found* | calc.** | d*** |
| thiacloprid | 3 | 60 | | 6 |
| (I) | 500 | 0 | | 6 |
| thiacloprid + (I) (1:167) | 3 + 500 | 85 | 60 | 6 |
| clothianidin | 0.6 | 60 | | 6 |
| (I) | 500 | 0 | | 6 |
| clothianidin + (I) (1:833) | 0.6 + 500 | 98 | 60 | 6 |
| thiamethoxam | 0.6 | 85 | | 1 |
| (I) | 100 | 0 | | 1 |
| thiamethoxam + (I) (1:167) | 0.6 + 100 | 90 | 85 | 1 |
| dinotefuran | 3 | 15 | | 1 |
| (I) | 100 | 0 | | 1 |
| dinotefuran + (I) (1:33) | 3 + 100 | 35 | 15 | 1 |

*found = activity found
**calc. = activity calculated using Colby's formula
***d = evaluation after the given number of days Example C

| *Phaedon* larvae test | |
|---|---|
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration. Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed. The determined kill rates are calculated using Colby's formula (see page 29).

In this test, for example, the following active compound combination according to the present application shows a synergistically enhanced activity, compared to the active compounds applied on their own:

TABLE C

| | Plant-damaging insects *Phaedon* larvae test | | | |
|---|---|---|---|---|
| | Concentration of active | Kill rate in % after d | | |
| Active compounds | compound in ppm | found* | calc.** | d*** |
| thiacloprid | 15 | 85 | | 6 |
| (I) | 3 | 70 | | 6 |
| thiacloprid + (I) (5:1) | 15 + 3 | 100 | 95.5 | 6 |
| triflumuron | 0.6 | 0 | | 6 |
| (I) | 0.12 | 0 | | 6 |
| triflumuron + (I) (5:1) | 0.6 + 0.12 | 70 | 0 | 6 |

TABLE C-continued

|  | Plant-damaging insects Phaedon larvae test | | | |
|---|---|---|---|---|
|  | Concentration of active | Kill rate in % after d | | |
| Active compounds | compound in ppm | found* | calc.** | d*** |
| thiamethoxam | 15 | 85 |  | 3 |
| (I) | 3 | 60 |  | 3 |
| thiamethoxam + (I) (5:1) | 15 + 3 | 100 | 94 | 3 |
| emamectin-benzoate | 0.006 | 10 |  | 6 |
| (I) | 0.12 | 0 |  | 6 |
| emamectin-benzoate + (I) (1:20) | 0.006 + 0.12 | 100 | 10 | 6 |
| flufenoxuron | 3 | 0 |  | 3 |
| (I) | 0.6 | 0 |  | 3 |
| flufenoxuron + (I) (5:1) | 3 + 0.6 | 95 | 0 | 3 |
| abamectin | 0.12 | 25 |  | 3 |
| (I) | 0.6 | 0 |  | 3 |
| abamectin + (I) (1:5) | 0.12 + 0.6 | 80 | 25 | 3 |
| indoxacarb | 0.6 | 35 |  | 3 |
| (I) | 0.12 | 0 |  | 3 |
| indoxacarb + (I) (5:1) | 0.6 + 0.12 | 100 | 35 | 3 |

*found. = activity found
**calc. = activity calculated using Colby's formula
***d = evaluation after the given number of days Example D

| Plutella test, resistant strain | |
|---|---|
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (Brassica oleracea) are treated by being dipped into the preparation of active compound of the desired concentration and are populated with caterpillars of the diamondback moth (Plutella xylostella, resistant strain) while the leaves are still moist.

After the desired period of time, the kill in % is determined. 100% means that all caterpillars have been killed; 0% means that none of the caterpillars have been killed. The determined kill rates are calculated using Colby's formula (see page 29).

In this test, for example, the following active compound combination according to the present application shows a synergistically enhanced activity, compared to the active compounds applied on their own:

TABLE D

|  | Plant-damaging insects Plutella test, resistant strain | | | |
|---|---|---|---|---|
|  | Concentration | Kill rate in % after d | | |
| Active compounds | of active compound in ppm | found* | calc.** | d*** |
| thiacloprid | 3 | 5 |  | 3 |
| (I) | 0.024 | 70 |  | 3 |
| thiacloprid + (I) (125:1) | 3 + 0.024 | 100 | 71.5 | 3 |
| triflumuron | 3 | 0 |  | 6 |
| (I) | 0.024 | 30 |  | 6 |
| triflumuron + (I) (125:1) | 3 + 0.024 | 75 | 30 | 6 |
| (I) | 0.02 | 30 |  | 6 |
| methoxyfenozide | 0.6 | 0 |  | 6 |
| (I) + methoxyfenozide (1:30) | 0.02 + 0.6 | 50 | 30 | 6 |
| thiamethoxam | 3 | 0 |  | 6 |
| (I) | 0.024 | 90 |  | 6 |
| thiamethoxam + (I) (125:1) | 3 + 0.024 | 95 | 90 | 6 |
| emamectin-benzoate | 0.00024 | 15 |  | 6 |
| (I) | 0.0048 | 10 |  | 6 |
| emamectin-benzoate + (I) (1:20) | 0.00024 + 0.0048 | 85 | 23.5 | 6 |
| flufenoxuron | 0.12 | 40 |  | 6 |
| (I) | 0.0048 | 0 |  | 6 |
| flufenoxuron + (I) (25:1) | 0.12 + 0.0048 | 100 | 40 | 6 |
| indoxacarb | 0.12 | 50 |  | 6 |
| (I) | 0.024 | 85 |  | 6 |
| indoxacarb + (I) (5:1) | 0.12 + 0.024 | 100 | 92.5 | 6 |

*found = activity found
**calc. = activity calculated using Colby's formula
***d = evaluation after the given number of days

Example E

| Plutella test, sensitive strain | |
|---|---|
| Solvent: | 7 parts by weight of dimethylformamide |
| Emulsifier: | 2 parts by weight of alkylaryl polyglycol ether |

To produce a suitable preparation of active compound, I part by weight of active compound is mixed with the stated amounts of solvent and emulsifier, and the concentrate is diluted with emulsifier-containing water to the desired concentration.

Cabbage leaves (Brassica oleracea) are treated by being dipped into the preparation of active compound of the desired concentration and are populated with caterpillars of the diamondback moth (Plutella xylostella, sensitive strain) while the leaves are still moist.

After the desired period of time, the kill in % is determined. 100% means that all caterpillars have been killed; 0% means that none of the caterpillars have been killed. The determined kill rates are calculated using Colby's formula (see page 29).

In this test, for example, the following active compound combination according to the present application shows a synergistically enhanced activity, compared to the active compounds applied on their own:

| Active compounds | Concentration of active compound in ppm | Kill rate in % after d | | |
|---|---|---|---|---|
| | | found* | calc.** | d*** |
| triflumuron | 0.6 | 0 | | 3 |
| (I) | 0.0048 | 0 | | 3 |
| triflumuron + (I) (125:1) | 0.6 + 0.0048 | 100 | 0 | 3 |
| (I) | 0.0064 | 60 | | 6 |
| deltamethrin | 0.00128 | 40 | | 6 |
| (I) + deltamethrin (5:1) | 0.0064 + 0.00128 | 95 | 76 | 6 |
| (I) | 0.024 | 55 | | 3 |
| fipronil | 0.12 | 65 | | 3 |
| (I) + fipronil (1:5) | 0.024 + 0.12 | 100 | 84.25 | 3 |
| emamectin-benzoate | 0.00024 | 10 | | 6 |
| (I) | 0.0048 | 25 | | 6 |
| emamectin-benzoate + (I) (1:20) | 0.00024 + 0.0048 | 95 | 32.5 | 6 |
| flufenoxuron | 0.12 | 0 | | 3 |
| (I) | 0.0048 | 0 | | 3 |
| flufenoxuron + (I) (25:1) | 0.12 + 0.0048 | 85 | 0 | 3 |
| abamectin | 0.00096 | 35 | | 3 |
| (I) | 0.0048 | 0 | | 3 |
| abamectin + (I) (1:5) | 0.00096 + 0.0048 | 85 | 35 | 3 |
| indoxacarb | 0.024 | 0 | | 3 |
| (I) | 0.0048 | 0 | | 3 |
| indoxacarb + (I) (5:1) | 0.024 + 0.0048 | 65 | 0 | 3 |
| (I) | 0.032 | 65 | | 3 |
| spinosad | 0.0064 | 5 | | 3 |
| (I) + spinosad (5:1) | 0.032 + 0.0064 | 100 | 66.75 | 3 |

*found = activity found
**calc. = activity calculated using Colby's formula
***d = evaluation after the given number of days

Example F

| Heliothis armigera test | |
|---|---|
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Soyabean shoots (Glycine max) are treated by being dipped into the preparation of active compound of the desired concentration and are populated with Heliothis armigera caterpillars while the leaves are still moist.

After the desired period of time, the kill in % is determined. 100% means that all caterpillars have been killed; 0% means that none of the caterpillars have been killed. The determined kill rates are calculated using Colby's formula (see page 29).

In this test, for example, the following active compound combination according to the present application shows a synergistically enhanced activity, compared to the active compounds applied on their own:

TABLE F

Plant-damaging insects
Heliothis armigera test

| Active compounds | Concentration of active compound in ppm | Kill rate in % after d | | |
|---|---|---|---|---|
| | | found* | calc.** | d*** |
| clothianidin | 3 | 10 | | 3 |
| (I) | 0.024 | 80 | | 3 |
| clothianidin + (I) (125:1) | 3 + 0.024 | 90 | 82 | 3 |
| triflumuron | 15 | 0 | | 3 |
| (I) | 0.12 | 80 | | 3 |
| triflumuron + (I) (125:1) | 15 + 0.12 | 100 | 80 | 3 |
| (I) | 0.032 | 90 | | 4 |
| deltamethrin | 0.0064 | 10 | | 4 |
| (I) + deltamethrin (5:1) | 0.032 + 0.0064 | 100 | 91 | 4 |
| (I) | 0.1 | 80 | | 3 |
| methoxyfenozide | 3 | 50 | | 3 |
| (I) + methoxyfenozide (1:30) | 0.1 + 3 | 100 | 90 | 3 |
| (I) | 0.024 | 70 | | 6 |
| fipronil | 0.12 | 10 | | 6 |
| (I) + fipronil (1:5) | 0.024 + 0.12 | 80 | 73 | 6 |
| emamectin-benzoate | 0.00024 | 0 | | 6 |
| (I) | 0.0048 | 10 | | 6 |
| emamectin-benzoate + (I) (1:20) | 0.00024 + 0.0048 | 100 | 10 | 6 |
| flufenoxuron | 0.12 | 15 | | 6 |
| (I) | 0.0048 | 15 | | 6 |
| flufenoxuron + (I) (25:1) | 0.12 + 0.0048 | 75 | 27.75 | 6 |
| abamectin | 0.0048 | 30 | | 6 |
| (I) | 0.024 | 70 | | 6 |
| abamectin + (I) (1:5) | 0.0048 + 0.024 | 100 | 79 | 6 |
| indoxacarb | 0.024 | 0 | | 6 |
| (I) | 0.0048 | 0 | | 6 |
| indoxacarb + (I) (5:1) | 0.024 + 0.0048 | 50 | 0 | 6 |

*found = activity found
**calc. = activity calculated using Colby's formula
***d = evaluation after the given number of days

Example G

| | Spodoptera frugiperda test |
|---|---|
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the armyworm (*Spodoptera frugiperda*) while the leaves are still moist.

After the desired period of time, the kill in % is determined. 100% means that all caterpillars have been killed; 0% means that none of the caterpillars have been killed. The determined kill rates are calculated using Colby's formula (see page 29).

In this test, for example, the following active compound combination according to the present application shows a synergistically enhanced activity, compared to the active compounds applied on their own:

TABLE G

Plant-damaging insects
*Spodoptera frugiperda* test

| Active compounds | Concentration of active compound in ppm | Kill rate in % after d found* | calc.** | d*** |
|---|---|---|---|---|
| triflumuron | 0.12 | 5 | | 3 |
| (I) | 0.024 | 70 | | 3 |
| triflumuron + (I) (5:1) | 0.12 + 0.024 | 85 | 71.5 | 3 |
| ethiprole | 20 | 10 | | 6 |
| (I) | 0.16 | 95 | | 6 |
| ethiprole + (I) (125:1) | 20 + 0.16 | 100 | 95.5 | 6 |
| (I) | 0.16 | 70 | | 4 |
| deltamethrin | 0.0064 | 0 | | 4 |
| (I) + deltamethrin (25:1) | 0.16 + 0.0064 | 100 | 70 | 4 |
| (I) | 0.02 | 5 | | 6 |
| methoxyfenozide | 0.6 | 5 | | 6 |
| (I) + methoxyfenozide (1:30) | 0.02 + 0.6 | 70 | 9.75 | 6 |
| (I) | 0.12 | 50 | | 3 |
| fipronil | 0.6 | 20 | | 3 |
| (I) + fipronil (1:5) | 0.12 + 0.6 | 80 | 60 | 3 |
| dinotefuran | 3 | 40 | | 3 |
| (I) | 0.024 | 35 | | 3 |
| dinotefuran + (I) (125:1) | 3 + 0.024 | 80 | 61 | 3 |
| emamectin-benzoate | 0.006 | 70 | | 3 |
| (I) | 0.12 | 30 | | 3 |
| emamectin-benzoate + (I) (1:20) | 0.006 + 0.12 | 100 | 79 | 3 |
| abamectin | 3 | 25 | | 3 |
| (I) | 0.12 | 35 | | 3 |
| abamectin + (I) (25:1) | 3 + 0.12 | 100 | 51.25 | 3 |
| indoxacarb | 0.6 | 60 | | 3 |
| (I) | 0.12 | 25 | | 3 |
| indoxacarb + (I) (5:1) | 0.6 + 0.12 | 100 | 70 | 3 |
| (I) | 0.16 | 70 | | 3 |
| spinosad | 0.032 | 35 | | 3 |
| (I) + spinosad (5:1) | 0.16 + 0.032 | 100 | 80.5 | 3 |

*found = activity found
**calc. = activity calculated using Colby's formula
***d = evaluation after the given number of days

Example H

| | Spodoptera exigua test |
|---|---|
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the armyworm (*Spodoptera exigua*) while the leaves are still moist.

After the desired period of time, the kill in % is determined. 100% means that all caterpillars have been killed; 0% means that none of the caterpillars have been killed. The determined kill rates are calculated using Colby's formula (see page 29).

In this test, for example, the following active compound combination according to the present application shows a synergistically enhanced activity, compared to the active compounds applied on their own:

TABLE H

Plant-damaging insects
*Spodoptera exigua* test

| Active compounds | Concentration of active compound in ppm | Kill rate in % after d found* | calc.** | d*** |
|---|---|---|---|---|
| triflumuron | 15 | 15 | | 3 |
| (I) | 0.12 | 40 | | 3 |
| triflumuron + (I) (125:1) | 15 + 0.12 | 100 | 49 | 3 |
| (I) | 0.032 | 10 | | 4 |
| deltamethrin | 0.00128 | 0 | | 4 |
| (I) + deltamethrin (25:1) | 0.032 + 0.00128 | 80 | 10 | 4 |
| emamectin-benzoate | 0.0012 | 20 | | 6 |
| (I) | 0.024 | 40 | | 6 |
| emamectin-benzoate + (I) (1:20) | 0.0012 + 0.024 | 100 | 52 | 6 |
| flufenoxuron | 0.6 | 0 | | 3 |
| (I) | 0.12 | 40 | | 3 |
| flufenoxuron + (I) (5:1) | 0.6 + 0.12 | 100 | 40 | 3 |
| abamectin | 3 | 70 | | 6 |
| (I) | 0.12 | 85 | | 6 |
| abamectin + (I) (25:1) | 3 + 0.12 | 100 | 95.5 | 6 |
| indoxacarb | 0.6 | 20 | | 3 |
| (I) | 0.12 | 0 | | 3 |
| indoxacarb + (I) (5:1) | 0.6 + 0.12 | 100 | 20 | 3 |

*found = activity found
**calc. = activity calculated using Colby's formula
***d = evaluation after the given number of days

Example I

Critical Concentration Test/soil Insects—Treatment of Transgenic Plants

| Test insect: | *Diabrotica balteata* - larvae in soil |
|---|---|
| Solvent: | 7 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. Here, the concentration of active compound in the preparation is virtually irrelevant; only the amount by weight of active compound per volume unit of soil, which is stated in ppm (mg/l) matters. 0.25 l pots are filled with the soil and allowed to stand at 20° C.

Immediately after preparation, 5 pre-germinated maize corns of the cultivar YIELD GUARD (trademark of Monsanto Comp., USA) are placed into each pot. After 2 days, the corresponding test insects are placed into the treated soil. After a further 7 days, the efficacy of the active compound is determined by counting the maize plants that have emerged (1 plant=20% efficacy).

Example K

| *Heliothis virescens* test - treatment of transgenic plants | |
|---|---|
| Solvent: | 7 parts by weight of acetone |
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Soyabean shoots (*Glycine max*) of the cultivar Roundup Ready (trademark of Monsanto Comp. USA) are treated by being dipped into the preparation of active compound of the desired concentration and are populated with the tobacco bollworm *Heliothis virescens* while the leaves are still moist.

After the desired period of time, the kill of the insects is determined.

What is claimed is:

1. A composition comprising a mixture of
(a) N²-[1,1-dimethyl-2-(methylsulphonyl)ethyl]-3-iodo-N¹-{2-methyl-4-[1,2,2,2-tetrafluoro-1-(trifluoromethyl)ethyl]phenyl}phthalamide of formula (I)

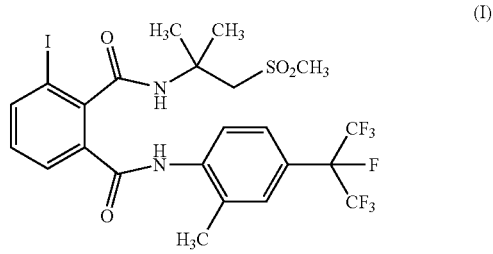

and
(b) one or more compounds selected from the group consisting of triflumuron at a ratio of component (a) to triflumuron of 10:1 to 1:150, flufenoxuron at a ratio of component (a) to flufenoxuron of 10:1 to 1:50, methoxyfenozide at a ratio of component (a) to methoxyfenozide of 10:1 to 1:50, tebufenozide at a ratio of component (a) to tebufenozide of 10:1 to 1:50, deltamethrin at a ratio of component (a) to deltamethrin of 50:1 to 1:10, ethiprole at a ratio of component (a) to ethiprole of 10:1 to 1:150, fipronil at a ratio of component (a) to fipronil of 100:1 to 1:100, indoxacarb at a ratio of component (a) to indoxacarb of 100:1 to 1:100, emamectin-benzoate at a ratio of component (a) to emamectin-benzoate of 50:1 to 1:10, abamectin at a ratio of component (a) to abamectin of 50:1 to 1:100, and spinosad at a ratio of component (a) to spinosad of 50:1 to 1:10.

2. A method for controlling insects, arachnids, and mites comprising allowing an effective amount of a mixture of claim 1 to act on insects, arachnids, and mites and/or their habitat.

3. A process for preparing an insecticidal and acaricidal composition comprising mixing a mixture of claim 1 with extenders and/or surfactants.

* * * * *

UNITED STATES PATENT AND TRADEMARK OFFICE
CERTIFICATE OF CORRECTION

PATENT NO. : 7,288,572 B2
APPLICATION NO. : 11/521881
DATED : October 30, 2007
INVENTOR(S) : Jorg Konze et al.

It is certified that error appears in the above-identified patent and that said Letters Patent is hereby corrected as shown below:

In Col. 28, line 18
remove "(b) one or more compounds .... spinosad of 50:1 to 1:10."

Replace with --(b) one or more compounds selected from the group consisting of triflumuron at a weight ratio of component (a) to triflumuron of 10:1 to 1:150, flufenoxuron at a weight ratio of component (a) to flufenoxuron of 10:1 to 1:150, and methoxyfenozide at a weight ratio of component (a) to methoxyfenozide of 10:1 to 1:150.--

Signed and Sealed this

Twenty-fourth Day of June, 2008

JON W. DUDAS
*Director of the United States Patent and Trademark Office*